(12) United States Patent
Bogoni et al.

(10) Patent No.: US 10,949,975 B2
(45) Date of Patent: Mar. 16, 2021

(54) PATIENT MANAGEMENT BASED ON ANATOMIC MEASUREMENTS

(71) Applicant: Siemens Healthcare GmbH, Erlangen (DE)

(72) Inventors: Luca Bogoni, Philadelphia, PA (US); Marcos Salganicoff, Bala Cynwyd, PA (US); Matthias Wolf, Coatesville, PA (US); Shu Liao, Chester Springs, PA (US); Yiqiang Zhan, Berwyn, PA (US); Gerardo Hermosillo-Valadez, West Chester, PA (US); Xiang Sean Zhou, Exton, PA (US); Zhigang Peng, Ambler, PA (US)

(73) Assignee: Siemens Healthcare GmbH, Erlangen (DE)

( * ) Notice: Subject to any disclaimer, the term of this patent is extended or adjusted under 35 U.S.C. 154(b) by 727 days.

(21) Appl. No.: 15/088,305

(22) Filed: Apr. 1, 2016

(65) Prior Publication Data
US 2016/0300026 A1    Oct. 13, 2016

Related U.S. Application Data

(60) Provisional application No. 62/146,490, filed on Apr. 13, 2015, provisional application No. 62/153,643, filed on Apr. 28, 2015.

(51) Int. Cl.
*G16H 15/00* (2018.01)
*G06T 7/11* (2017.01)
(Continued)

(52) U.S. Cl.
CPC ............. *G06T 7/11* (2017.01); *A61B 5/055* (2013.01); *A61B 5/1075* (2013.01);
(Continued)

(58) Field of Classification Search
CPC ....... G06F 19/321; G06F 19/00; A61B 5/055; A61B 5/1075; A61B 5/4566; G16H 10/60;
(Continued)

(56) References Cited

U.S. PATENT DOCUMENTS

| 2007/0073195 A1* | 3/2007 | Chen | A61B 5/1075 600/594 |
| 2015/0112901 A1* | 4/2015 | Singer | A61B 5/7275 706/12 |
| 2015/0371390 A1* | 12/2015 | Gassner | G06T 7/10 382/128 |

OTHER PUBLICATIONS

Anderst, Baillargeon, Donaldson III, Lee, Kang, "Validation of a Non-Invasive Technique to Precisely Measure in Vivo Three-Dimensional Cervical Spine Movement", Mar. 15, 2011, National Institute of Health, 36(6): E393-E400 (Year: 2011).*

(Continued)

*Primary Examiner* — Robert A Sorey
*Assistant Examiner* — Kimberly A. Sass

(57) ABSTRACT

A framework for patient management based on anatomic measurements is described herein. In accordance with one aspect, patient records are clustered into a set of sub-populations based on first anatomic measurements and characteristics extracted from first patient data associated with a population of patients. A representative sub-population similar to a patient may be determined from the set of sub-populations based on the patient data of the patient. A report that presents the second anatomic measurements associated with the patient in relation to corresponding first anatomic measurements associated with the representative sub-population may then be generated.

8 Claims, 14 Drawing Sheets

(51) Int. Cl.
| | |
|---|---|
| *G06T 7/00* | (2017.01) |
| *A61B 5/00* | (2006.01) |
| *G16H 50/20* | (2018.01) |
| *G16H 10/60* | (2018.01) |
| *A61B 5/055* | (2006.01) |
| *A61B 5/107* | (2006.01) |
| *G16H 30/40* | (2018.01) |
| *G06N 3/04* | (2006.01) |

(52) U.S. Cl.
CPC .......... *A61B 5/4566* (2013.01); *G06T 7/0012* (2013.01); *G16H 10/60* (2018.01); *G16H 15/00* (2018.01); *G16H 30/40* (2018.01); *G16H 50/20* (2018.01); *G06N 3/04* (2013.01); *G06T 2207/10081* (2013.01); *G06T 2207/10116* (2013.01); *G06T 2207/20081* (2013.01); *G06T 2207/30012* (2013.01)

(58) Field of Classification Search
CPC .......... G16H 50/20; G16H 15/00; G06T 7/11; G06T 7/0012; G06T 2207/10081; G06T 2207/10116; G06T 2207/30012; G06T 2207/20081; G06N 3/08
USPC .......................................................... 705/3
See application file for complete search history.

(56) References Cited

OTHER PUBLICATIONS

Diaz-Parra, Arana, Moratal, "A Fully Automated Method for Spinal Cnaal Detection in Computed Tomography Images", 2014, Conf. Proc. IEEE Eng Med Biol Soc. (Year: 2014).*

Anderst, Lee, Donalson III, Kang, "Six-Degrees-of-Freedom Cervical Spine Range of Motion During Dynamic Flexion-Extension After Single-Level Anterior Arthodesis", 2013, J Bone Joint Surg Am. 2013;95:497-506 (Year: 2013).*

Tunset, Kjaer, Chreiteh, Jensen, "A method for quantitative measurement of lumbar intervertebral disc structures: an intra- and inter-rater agreement and reliability study", 2013, Chiropractic & Manual Therapies 2013, 21:26 (Year: 2013).*

Sholukha, Bonnechere, Salvia, Moiseev, Rooz, Van Sint Jan, "Model-based approach for human kinematics reconstruction from markerless and marker-based motion analysis systems", Jul. 26, 2013, Journal of Biomechanics 46 (2013) 2363-2371, (Year: 2013).*

Erbel R, Eggebrecht H, "Aortic dimensions and the risk of dissection," Heart, 2006;92(1):137-142.

Wang Y-L, Wang Q-L, Wang L, et al., "Body surface area as a key determinant of aortic root and arch dimensions in a population-based study," Experimental and Therapeutic Medicine. 2013;5(2):406-410.

Pearce et al., "Aortic diameter as a function of age, gender, and body surface area," Surgery, Oct. 1993;114(4)(Abstract only).

O'Rourke M, Farnsworth A, O'Rourke J., "Aortic Dimensions and Stiffness in Normal Adults," J Am Coll Cardiol Img, 2008;1(6):749-751.

* cited by examiner

PATIENT MANAGEMENT BASED ON ANATOMIC MEASUREMENTS

CROSS-REFERENCE TO RELATED APPLICATIONS

The present application claims the benefit of U.S. provisional application No. 62/146,490 filed Apr. 13, 2015 and U.S. provisional application No. 62/153,643 filed Apr. 28, 2015, the entire contents of which are herein incorporated by reference.

TECHNICAL FIELD

The present disclosure generally relates to medical data processing, and more particularly to patient management based on anatomic measurements.

BACKGROUND

The field of medical imaging has seen significant advances since the time X-Rays were first used to determine anatomic abnormalities. Medical imaging hardware has progressed in the form of newer machines such as Magnetic Resonance Imaging (MM) scanners, Computed Axial Tomography (CAT) scanners, etc. Because of the large amount of image data generated by such modern medical scanners, there has been and remains a need for developing image processing techniques that can automate some or all of the processes to determine the presence of anatomic abnormalities in scanned medical images.

Digital medical images are constructed using raw image data obtained from a scanner, for example, a CAT scanner, MRI, etc. Digital medical images are typically either a two-dimensional ("2D") image made of pixel elements or a three-dimensional ("3D") image made of volume elements ("voxels"). Such 2D or 3D images are processed using medical image recognition techniques to determine the presence of anatomic structures such as cysts, tumors, polyps, etc. Given the amount of image data generated by any given image scan, it is preferable that an automatic technique should point out anatomic features in the selected regions of an image to a doctor for further diagnosis of any disease or condition.

Automatic image processing and recognition of structures within a medical image is generally referred to as Computer-Aided Detection (CAD). A CAD system can process medical images and identify anatomic structures, including possible abnormalities, for further review. Such possible abnormalities are often called candidates and are considered to be generated by the CAD system based upon the medical images.

Technicians, radiologists and physicians typically perform anatomic measurements multiple times daily on medical images to assess the state of a specific anatomic structure and/or determine whether the measurements are within acceptable parameters. To enhance efficiency and reduce inter- and intra-reader variability, automated measurement tools have been designed for routine, as well as specialized, studies. However, such automated measurement tools are typically not available for measuring certain types of medical conditions.

One such medical condition is spondylolisthesis. Spondylolisthesis is one of the most common spinal diseases. It is caused by the anterior shift of one vertebra over its subjacent vertebra due to various causes such as fracture, degenerative disc, congenital reasons, etc. Patients with spondylolisthesis often suffer from severe lower back pain. The clinical workflow and treatment methods for spondylolisthesis may vary depending on how severe (i.e., the grade) the condition is. For instance, conservative treatment methods, such as physical therapy and resting, are often applied to patients with low-grade spondylolisthesis, while surgery may be necessary for patients with high-grade spondylolisthesis.

In current clinical workflows, anterior shift of the vertebra is manually measured to determine the degree of spondylolisthesis. Such manual measurements are time-consuming and typically not reproducible. Additionally, such measurements are often directly presented to the physician, without any reference to representative values to support patient management. The physician needs to rely on his or her own experience and knowledge to determine the correct course of action. At times, the physician may search the literature or web to identify the correct course of action. This is an inherent limitation in a busy clinical practice.

SUMMARY

Described herein is a framework for patient management based on anatomic measurements. In accordance with one aspect, patient records are clustered into a set of sub-populations based on first anatomic measurements and characteristics extracted from first patient data associated with a population of patients. The framework may then receive second patient data of a patient, wherein the second patient data comprises image data and associated second anatomic measurements of at least one structure of interest. A representative sub-population similar to the patient may then be determined from the set of sub-populations based on the second patient data. A report that presents the second anatomic measurements in relation to corresponding first anatomic measurements associated with the representative sub-population may be generated.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
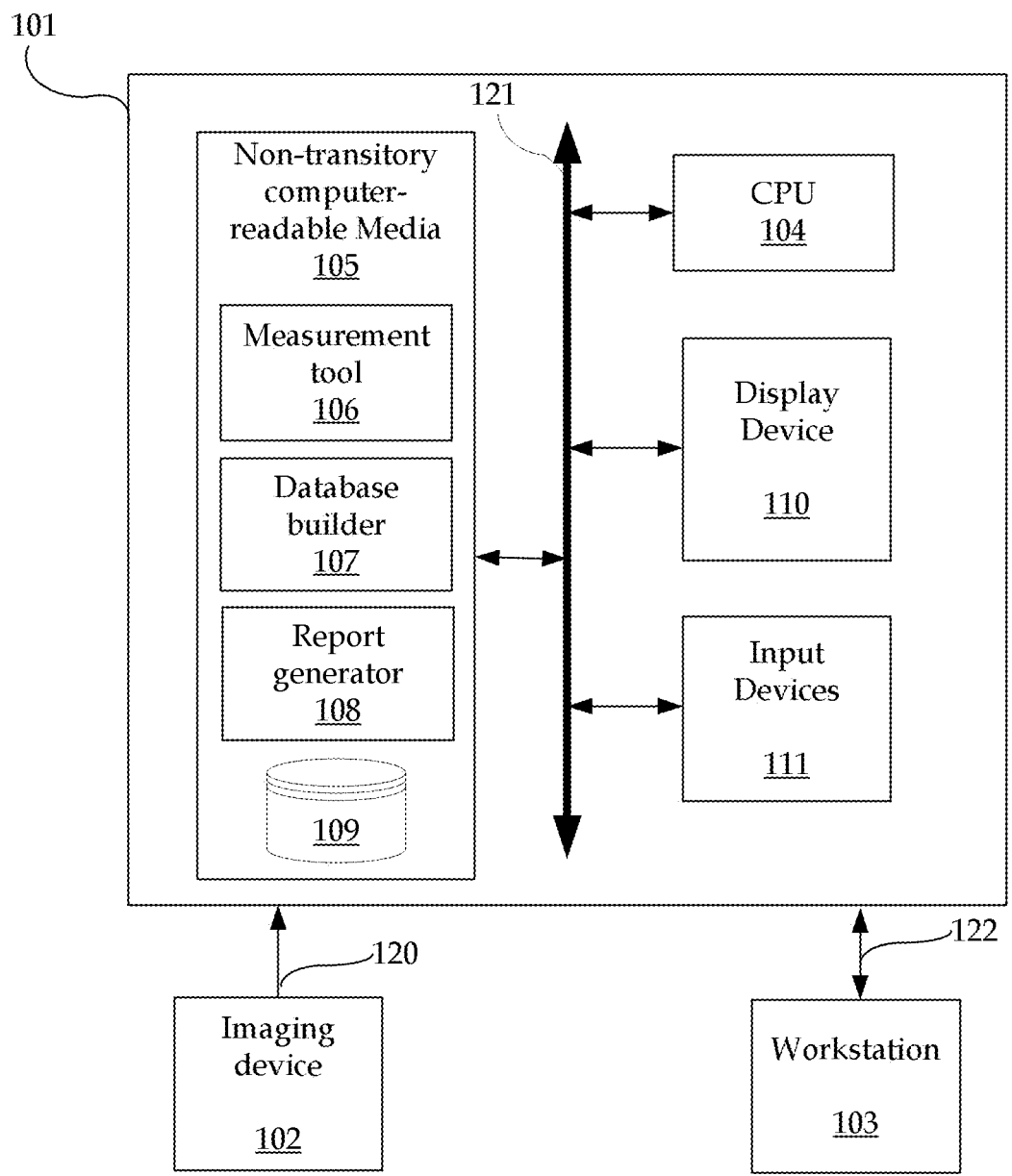
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3 Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

A framework for patient management based on anatomic measurements is described herein. In accordance with one aspect, the framework automatically determines the level of spondylolisthesis. More particularly, the framework automatically measures the anterior shift of one vertebra over its subjacent vertebra in the medical image data. The grade of spondylolisthesis may be determined based on established guidelines (e.g., Meyerding grading system).

In accordance with another aspect of the framework, anatomic measurements are performed in accordance with standard guidelines, and used to support patient management. The anatomic measurements of a given patient may be presented in relation to a representative sub-population of patients with similar characteristics and/or anatomic measurement values. In some implementations, the anatomic measurements are presented in relation to the anatomical measurements, characteristics, treatments, outcomes, and/or other information extracted from patient records associated with the representative sub-population.

By automating measurements, the present framework advantageously reduces intra- and inter-reader variability in performing measurements. Efficiency is improved by changing the role of the user (e.g., physician, radiologist) from performing a measurement to reviewing and verifying the measurements. Reporting aspects may be enhanced, since structured data can be automatically populated in case reports and sent to registries or other parties as needed. A more accurate view of the anatomy or disease may be provided. These and other exemplary advantages and features will be described in more details herein.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as imaging device 102 and workstation 103. In a networked deployment, computer system 101 may operate in the capacity of a server (e.g., thin-client server, such as syngo.Via® by Siemens Healthcare), a cloud computing platform, a client user machine in server-client user network environment, or as a peer machine in a peer-to-peer (or distributed) network environment.

In some implementations, computer system 101 comprises a processor or central processing unit (CPU) 104 coupled to one or more non-transitory computer-readable media 105 (e.g., computer storage or memory), display device 110 (e.g., monitor) and various input devices 111 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 105. In particular, the present techniques may be implemented by a measurement tool 106, a database builder 107, a report generator 108 and a database 109.

Non-transitory computer-readable media 105 may include random access memory (RAM), read-only memory (ROM), magnetic floppy disk, flash memory, and other types of memories, or a combination thereof. The computer-readable program code is executed by CPU 104 to process medical data retrieved from, for example, imaging device 102. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 109. Such data may also be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Imaging device 102 acquires medical image data 120 associated with at least one patient. Such medical image data 120 may be processed and stored in database 109. Imaging device 102 may be a radiology scanner (e.g., X-ray, MR or a CT scanner) and/or appropriate peripherals (e.g., keyboard and display device) for acquiring, collecting and/or storing such medical image data 120.

The workstation 103 may include a computer and appropriate peripherals, such as a keyboard and display device, and can be operated in conjunction with the entire system 100. For example, the workstation 103 may communicate directly or indirectly with the imaging device 102 so that the medical image data acquired by the imaging device 102 can be rendered at the workstation 103 and viewed on a display device. The workstation 103 may also provide other types of medical data 122 of a given patient currently undergoing examination. The workstation 103 may include a graphical user interface to receive user input via an input device (e.g., keyboard, mouse, touch screen voice or video recognition interface, etc.) to input the current medical data 122.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
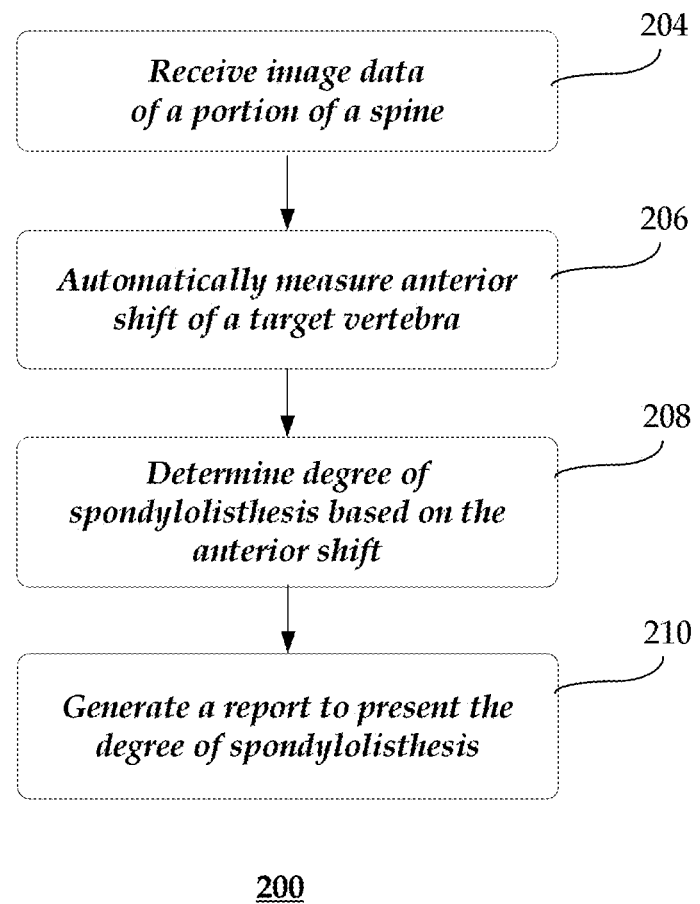
FIG. 2 shows an exemplary method of performing automated measurements by a computer system.

FIG. 2 shows an exemplary method 200 of performing automated measurements by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 204, measurement tool 106 receives image data of at least a portion of a spine (or vertebral column) of a given patient. The image data may be acquired from the patient by, for example, imaging device 102 using techniques such as magnetic resonance (MR) imaging, computed tomography (CT), helical CT, X-ray, angiography, positron emission tomography (PET), fluoroscopy, ultrasound, single photon emission computed tomography (SPECT), or a combination thereof.

At 206, measurement tool 106 automatically measures anterior shift of a target vertebra. The target vertebra is any vertebra along the spine that is identified for further study. The anterior shift generally refers to an acquired anterior displacement of the target vertebra relative to another structure (e.g., adjacent or subjacent vertebra).

In some implementations, measurement tool 106 automatically measures the anterior shift by measuring the displacement of the target vertebra relative to another anatomical structure. In another implementation, measurement tool 106 automatically measures the anterior shift by applying a deep learning technique to determine centroids of the vertebrae, vertebra-center coordinate systems or vertebra-specific landmarks, and determining the relative displacement of a vertebra with respect to its adjacent vertebra based on the centroids, vertebra-centers or vertebra-specific landmarks. In yet another implementation, the overall spine profile may be characterized (e.g. by a centerline or deep learning), and the anterior shift (or amount of spondylolisthesis) may be determined based on a deformation of the overall spine profile. This is especially useful in determining the overall shape or posture and identifying incremental changes.

Figure 3:
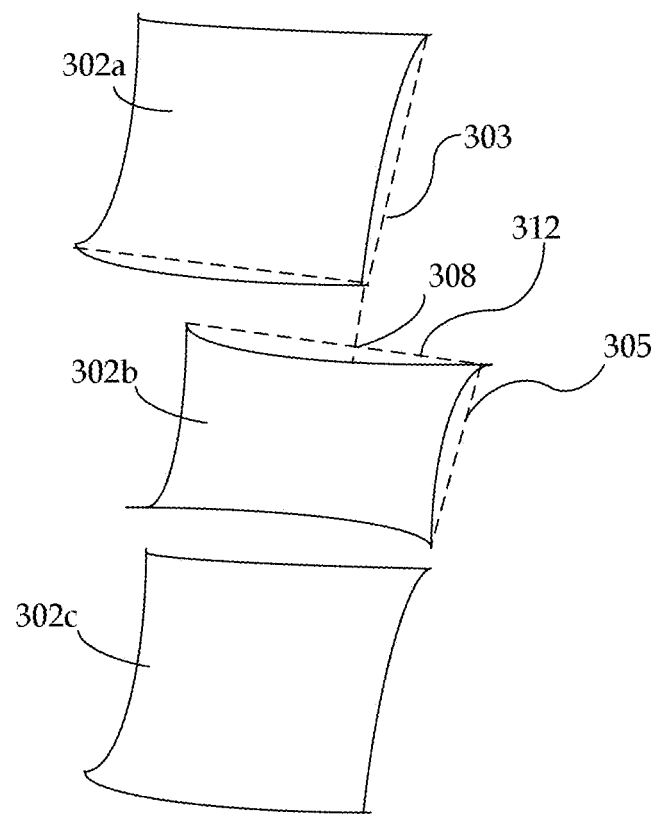
FIG. 3 illustrates an exemplary automatic measurement of anterior shift.

In some implementations, measurement tool 106 automatically measures the anterior shift of the target vertebra by identifying the front (or back) planes of the target and adjacent vertebrae, wherein the front (or back) planes are perpendicular to the plane of the spinal disc between the vertebrae. The anterior shift may then be determined by the distance between the front (or back) planes. FIG. 3 illustrates an exemplary automatic measurement of anterior shift. Three vertebrae 302*a-c* are shown for illustration purposes. The measurement tool 106 may first identify the front plane 303 of the target vertebra 302*a*, and the front plane 305 of the subjacent vertebra 302*b*. The anterior shift 312 of one vertebra 302*a* over its subjacent vertebra 302*b* may be obtained by the distance 312 between the front plane 303 and the front plane 305.

In yet other implementations, measurement tool 106 automatically measures the anterior shift by segmenting the target vertebra and its adjacent (e.g., subjacent) vertebra in the image data and determining the displacement of a point on the lower (or upper) surface of the target vertebra relative to a point on the upper (or lower) surface of the adjacent vertebra. To segment the target and adjacent vertebrae, the measurement tool 106 automatically detects pre-defined key landmarks of the spine. Such landmarks are pre-defined at key locations (e.g., center of each vertebra) to characterize anatomic and topological information of the spine. The landmarks may be detected by a machine learning-based engine that has been trained offline with a set of pre-defined training images. Based on the detected landmarks, a region of interest (ROI) containing a vertebra of the spine may be extracted. Accordingly, each vertebra of the spine may be segmented without the confusion caused by its adjacent vertebrae. The segmentation process may automatically generate semantic labels that identify the segmented vertebrae, such as cervical, thoracic and/or lumbar vertebra labels.

A multi-atlas segmentation scheme may also be performed. The vertebrae in the training images may be manually segmented to build a set of vertebral atlases for training the engine. Each vertebral atlas is registered to the target vertebra. The transformation model may be based on rigid, affine, or deformable transformations. After registration, intelligent fusion methods may be applied to derive the final segmentation results on the target and adjacent vertebrae based on the registered atlases. The fusion method may be, for example, a majority voting technique or a non-local mean-based label fusion technique.

Figure 4:
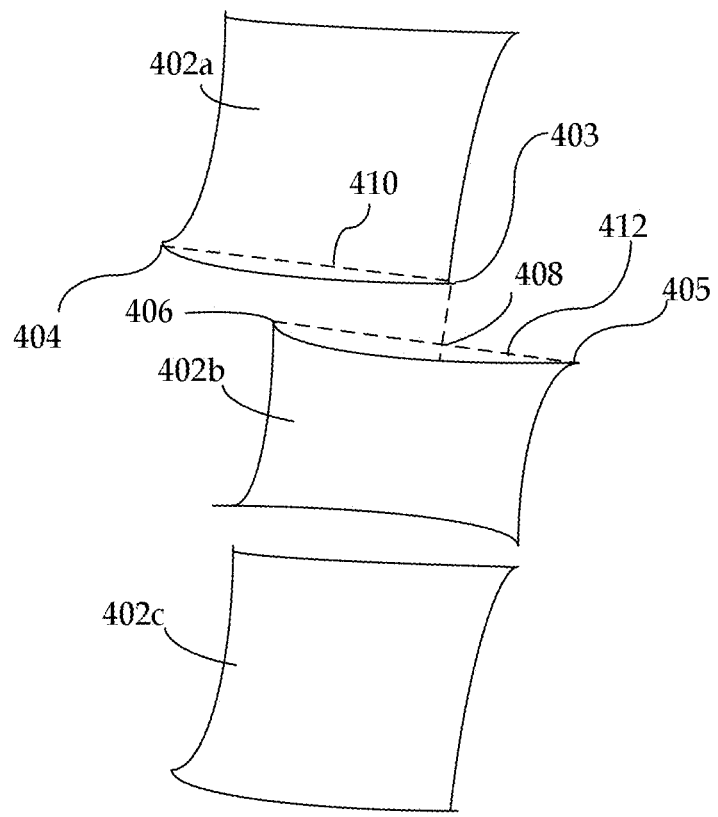
FIG. 4 illustrates another exemplary automatic measurement of anterior shift.

FIG. 4 illustrates another exemplary automatic measurement of anterior shift. Three segmented vertebrae 402*a-c* are shown for illustration purposes. The measurement tool 106 may first identify the most anterior point 404 and the most posterior point 403 of the lower surface of target vertebra 402*a*, and the most anterior point 406 and most posterior point 405 of the upper surface of the subjacent vertebra 302*b*. The anterior shift 412 of one vertebra 402*a* over its subjacent vertebra 402*b* may be obtained by projecting its most posterior point 403 on its lower surface to the upper surface of its subjacent vertebra 402*b*, and calculating the distance 412 between the projected point 408 and the most posterior point 405 on the upper surface of the subjacent vertebra 402*b*. The percentage of anterior shift (or slippage) may be determined by calculating the ratio of the anterior shift distance 412 to the distance between the most anterior point 406 and the most posterior point 405 on the upper surface of the subjacent vertebra.

Returning to FIG. 2, at 208, measurement tool 106 determines a degree of spondylolisthesis based on the anterior shift. In some implementations, the degree of spondylolisthesis is classified using the Meyerding grading system. The Meyerding grading system quantifies the degree of spondylolithesis based on the percentage of anterior shift of the vertebrae relative to its subjacent one (i.e., slippage). The Meyerding grading system has four different grades: (1) Grade 1: <25% slippage; (2) Grade 2: 25-50% slippage; (3) Grade 3: 50-75% slippage; and (4) Grade 4: >75% slippage. The appropriate grade may be assigned based on the shift percentage according to the Meyerding grading system.

At 210, report generator 108 generates a report to present the degree of spondylolisthesis. The report may be displayed at, for example, workstation 103. The report may include the measurements presented in an image that is anatomically aligned to the anatomic structure, and adjusted to account for appropriate viewing conditions. In addition, the report may be presented in relation to a representative sub-population of patients with similar characteristics (e.g., anterior shift, degree of spondylolisthesis) as the patient, as will be described in more details with reference to FIG. 10.

Figure 5:
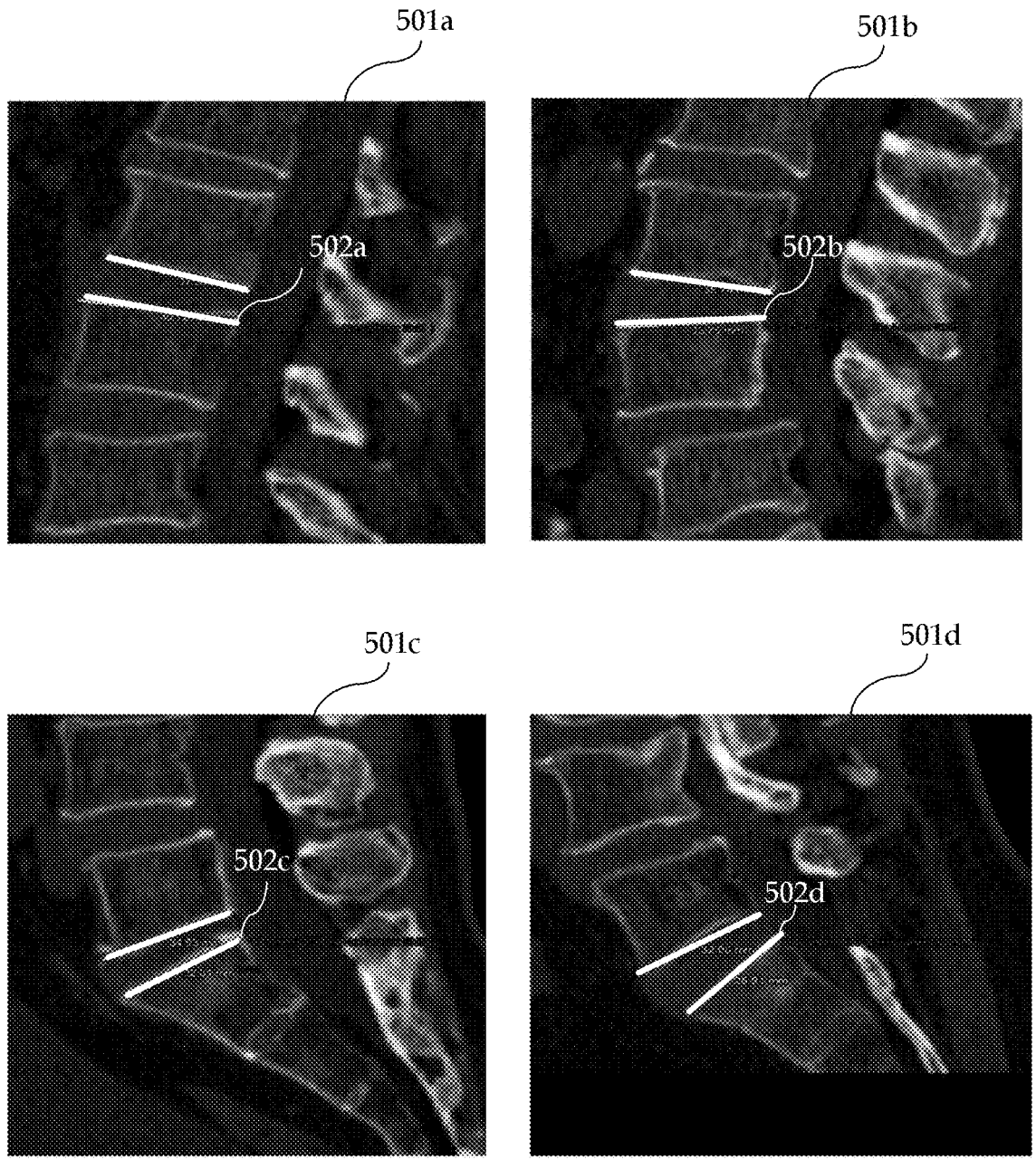
FIG. 5 shows exemplary medical images illustrating automatic measurements of anterior shift for normal patients.

FIG. 5 shows exemplary medical images 501*a-d* illustrating automatic measurements of anterior shift 502*a-d* for patients with normal spines. Such images 501*a-d* may be presented in the report generated by report generator 108 to illustrate the measurements of anterior shift. As shown, there is no anterior shift 502*a-d* for the normal spines shown in the images 501*a-d*.

Figure 6:
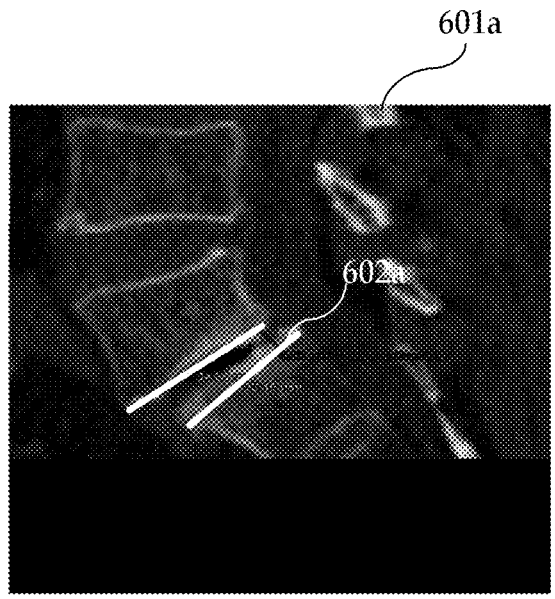
FIG. 6 shows exemplary medical images illustrating automatic measurements of anterior shift for grade 1 spondylolisthesis patients.
Figure 6:
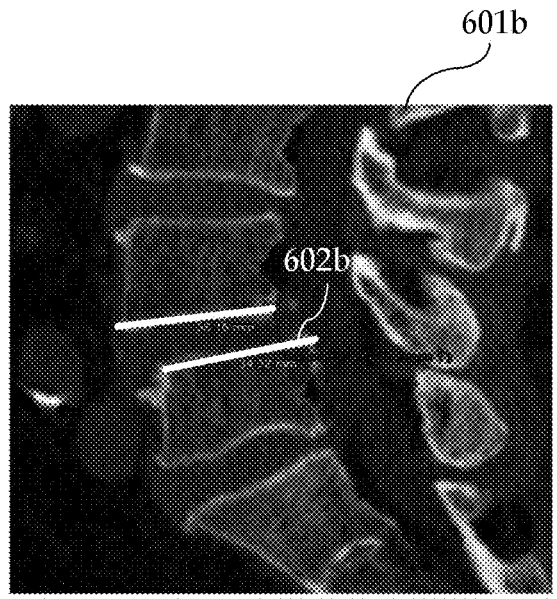
Figure 6:
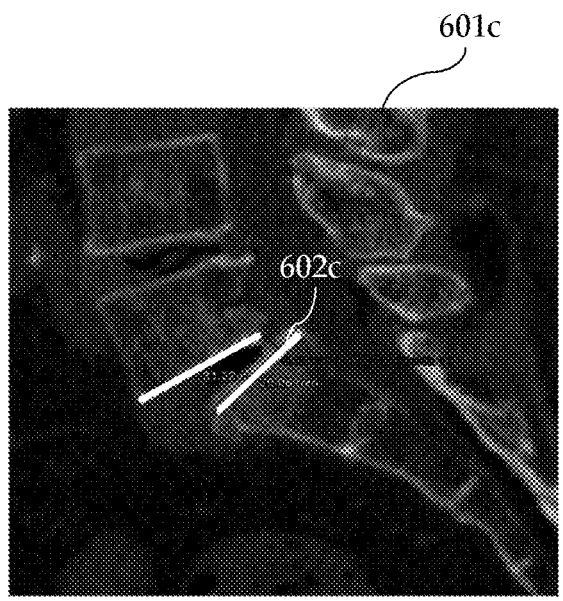
Figure 6:
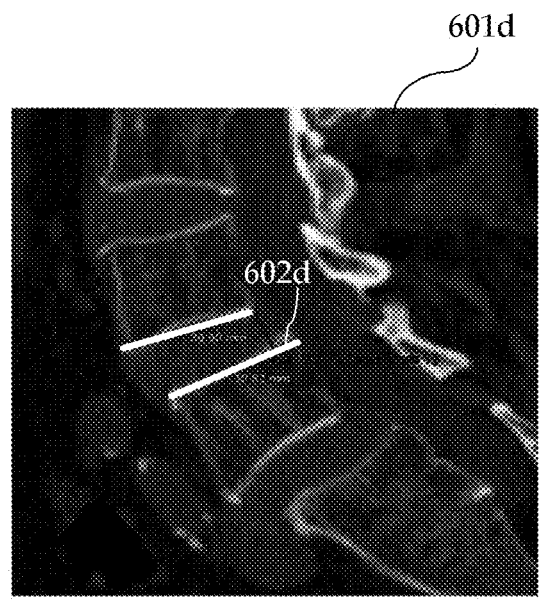

FIG. 6 shows exemplary medical images 601*a-d* illustrating automatic measurements of anterior shift 602*a-d* for grade 1 spondylolisthesis patients. Such images 601*a-d* may be presented in the report generated by report generator 108 to illustrate the measurements of anterior shift. As shown, the percentage of anterior shift are 15.51%, 21.66%, 19.67% and 14.95% for images 601*a*, 601*b*, 601*c* and 601*d* respectively.

Figure 7:
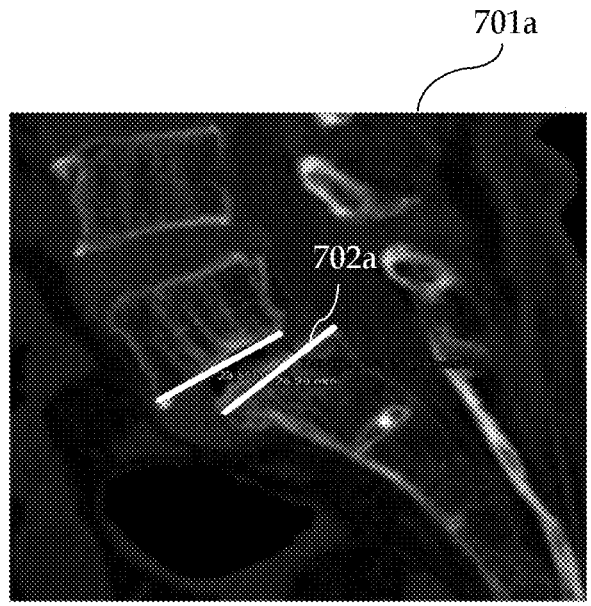
FIG. 7 shows exemplary medical images illustrating automatic measurements of anterior shift for grade 2 spondylolisthesis patients.
Figure 7:
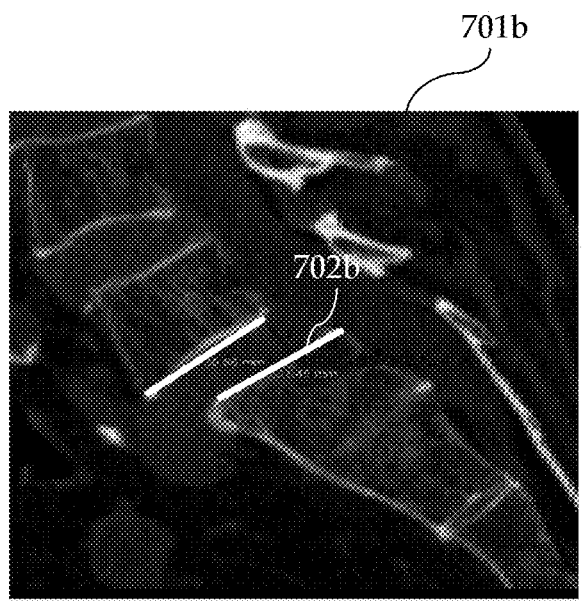

FIG. 7 shows exemplary medical images 701*a-b* illustrating automatic measurements of anterior shift 702*a-b* for grade 2 spondylolisthesis patients. Such images 701*a-b* may be presented in the report generated by report generator 108 to illustrate the measurements of anterior shift. As shown, the percentage of anterior shift are 27.57% and 35.47% for images 701*a* and 701*b* respectively.

The use of automated measurement tools, in routine as well as specialized study, allows for increase in efficiency, reduction in inter- and intra-reader variability, and archival of quantitative information as structured data for future analysis. Once validated by a physician, the structured data becomes the basis for implementing effective and efficient patient management decisions. Automated measurement tools enable quantification of the clinical condition or disease that is repeatable and consistent, enabling assessment of change of the condition or disease over time. Thus, automated anatomic measurements enables quantitative assessments of an onset of a disease or provide a means to quantify the growth of pathology that can be trended for the specific patient in the context of a larger population of patients. Automated measurements can be used by surgeons to, for example, select proper surgical devices. Automated three-dimensional (3D) measurement tools may also be directly provided to the surgeon, unlike in current workflows where surgeons only have access to two-dimensional (2D) images, from which the measurements may not reflect the 3D truth.

Figure 8:
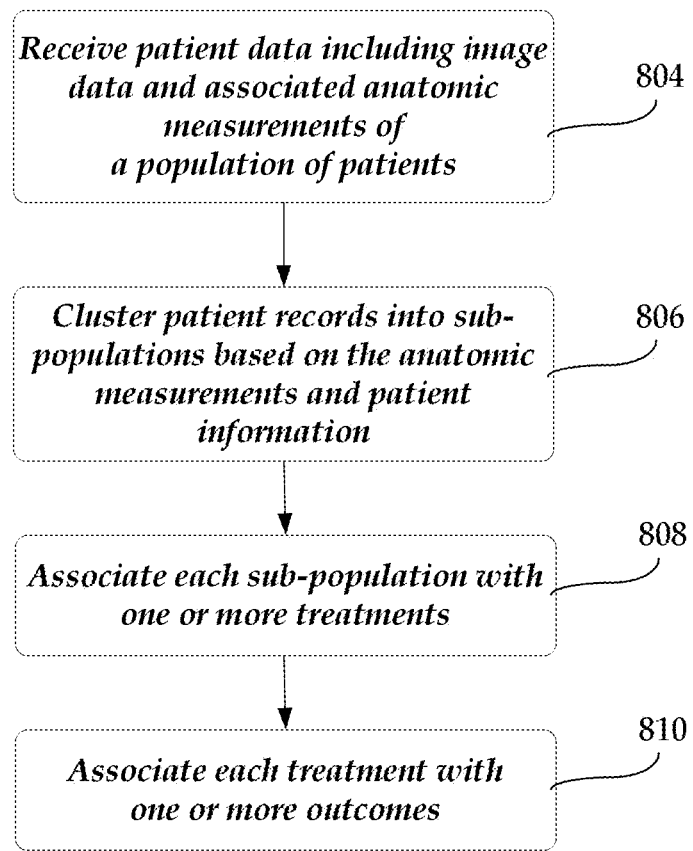
FIG. 8 shows an exemplary method of building a database by a computer system.

FIG. 8 shows an exemplary method 800 of building a database 109 by a computer system. It should be understood that the steps of the method 800 may be performed in the order shown or a different order. Additional, different, or fewer steps may also be provided. Further, the method 800 may be implemented with the system 101 of FIG. 1, a different system, or a combination thereof.

At 804, database builder 107 receives patient data of a population of patients. The number of patients in the sample population may range from a few thousands to millions. The patient data may include image data and associated anatomic measurements of at least one structure of interest, as well as other patient information. The image data may be acquired by, for example, imaging device 102, using techniques such as magnetic resonance (MR) imaging, computed tomography (CT), helical CT, X-ray, angiography, positron emission tomography (PET), fluoroscopy, ultrasound, single photon emission computed tomography (SPECT), or a combination thereof. Patient information may include, but is not limited to, patient history, examination reports, demographic information (e.g., ethnicity), specific patient information (e.g., age, gender, body mass index or BMI, weight, cholesterol level, allergy, test results, smoking, substance use, family history), risk factors or a combination thereof. Characteristics of the patient may be extracted from such patient information.

The anatomic measurements may one-dimensional, two-dimensional, three-dimensional, or other dimensional. The anatomic measurements may be performed on different structures of interest, such as at least a portion of the spine, heart, aorta, blood vessel, skeleton, muscle, nervous system, kidney, and so forth. In addition, different types of measurements may be performed. Exemplary measurements include, but are not limited to, diameter, length, thickness, area, volume, flow, change, and/or rate of change of measurements. For example, measurements may be performed to determine the anterior shift of one vertebra over its subjacent vertebra and/or the degree of spondylolisthesis, as previously described with reference to FIG. 2. The measurements may also be determined based on relationships between different base measurements, including but not limited to, angles, ratios, and so forth.

The anatomic measurements may have been performed either manually, semi-automatically or automatically. In some implementations, the patient data is automatically processed by measurement tool 106 to generate all available measurement values, such as the dimensions of bones in the body and relationships between them, dimensions and characteristics of organs, measurements of the complete anatomic system (e.g., respiratory, nervous system, etc.). The anatomic measurements may be performed based on anatomic landmarks pre-defined according to well-established guidelines (e.g., American College of Cardiology (ACC) and the American Heart Association (AHA) pocket guidelines for diagnosis and management of patient with thoracic aortic disease). Alternatively, or additionally, the anatomic measurements may be performed along a continuum of locations throughout the structure of interest. By supplying not only information at specific data points, but in a continuum of locations (as applicable), potential sources or onset of diseases may be revealed. These sources may be missed by measuring only at the discrete or pre-specified locations.

The anatomic measurements may be performed to, for example, assess the state of a specific anatomic structure and determine: whether the measurement values are within acceptable ranges according to demographic characteristics (e.g., ethnicity) and/or specific patient characteristics (e.g., age, gender, body mass index, smoking, substance use, family history); whether the measurements are impacted by risk factors originating from environmental or working conditions; or whether the measurements have changed since the prior examination and whether the change is significant given the patient characteristics or risk factors.

At 806, database builder 107 clusters patient records into sub-populations based on the anatomic measurements and/or characteristics extracted from the patient data. The patient records in each sub-population are more similar with respect to anatomic measurement values and/or characteristics to each other than those in other sub-populations thereof. Machine learning-based techniques may be employed to cluster the patient records into meaningful sub-populations. In some implementations, the machine learning techniques include a deep learning algorithm based on, for example, deep neural networks, convolutional deep neural networks, deep belief networks and recurrent neural networks. The patient records may be clustered according to, for example, diseases or clinical field of interest (e.g., cardiology, neurology, nephrology, etc.) determined by the type (or location) of the structures of interest measured by the anatomic measurements. The patient records may also be clustered with respect to the degree of condition or disease (e.g., spondylolisthesis grade) or range of values derived from the anatomic measurements. The patient records may further be clustered with respect to characteristics (e.g., ethnicity, age, gender, BMI, risk factor) extracted from the patient information.

At 808, database builder 107 associates each sub-population with one or more treatments. The one or more treatments (or therapies) may have been performed during prior patient management as evidenced by the patient information associated with the population of patients. The information of such prior treatments may be extracted from, for example, patient history records or examination reports associated with the patients. Exemplary treatments include, but are not limited to, surgery, medication, radiation, hormone replacement, ablation, chemotherapy, physical therapy, and so forth. The mapping information that relates the sub-populations to their respective treatments may be stored in, for example, a table, index file or other suitable data structure in database 109.

At 810, database builder 107 associates each treatment with one or more outcomes. The one or more outcomes have resulted from performing the associated treatment (or therapy) during previous patient management. Information of such previous treatments may be extracted from, for example, patient history. Each outcome indicates the effectiveness of the associated treatment. For example, the outcome may indicate that the disease or condition is cured, in complete remission, partial remission, improved, stable or refractory. Other types of outcomes may also be predefined. The mapping information that relates the treatments to the outcomes may be stored in, for example, a table, index file or other suitable data structure stored in database 109. Outcomes can not only be associated with individual subpopulations of patients, but can also be related to clinical studies that provide peer-reviewed analysis for a cohort of patients.

The creation of sub-populations and mapping of therapies to outcomes may be informed by published literature (e.g., peer-reviewed publications and meta-analyses). In some implementations, such information (e.g., mapping) is automatically extracted by a text processing unit which parses the literature document searching for specific information or keywords. This is an evolution of the automation of diagnostic report reading to understand and extract information such as therapies and outcomes. Alternatively, the mapping information is semi-automatically or manually incorporated by specialized experts. The use of published literature can prove to be of substantial value from an evidence-based medicine perspective, when associating therapies to outcomes.

Figure 9:
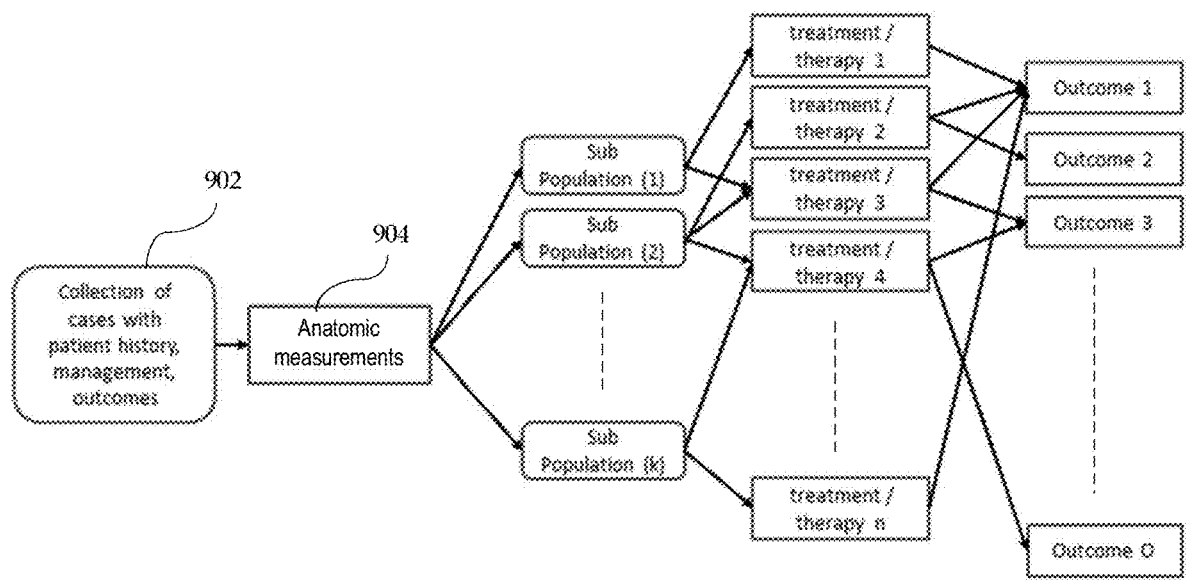
FIG. 9 shows an exemplary clustering of a collection of patient records.

FIG. 9 shows an exemplary clustering of a collection of patient records 902. By processing large collections of patients, anatomic measurements may be associated with risk factors and related to subpopulations, therapies and outcomes. As shown, anatomic measurements 904 are derived for a large collection of cases. The patient records associated with the anatomic measurements 904 are clustered into sub-populations (1) to (k) with respect to, for example, clinical area of interest and patient characteristics. Based on patient history, sub-populations (1) to (k) are mapped to treatments (or therapies) (1) to (n), which are then mapped to outcomes (1) to (O).

Figure 10:
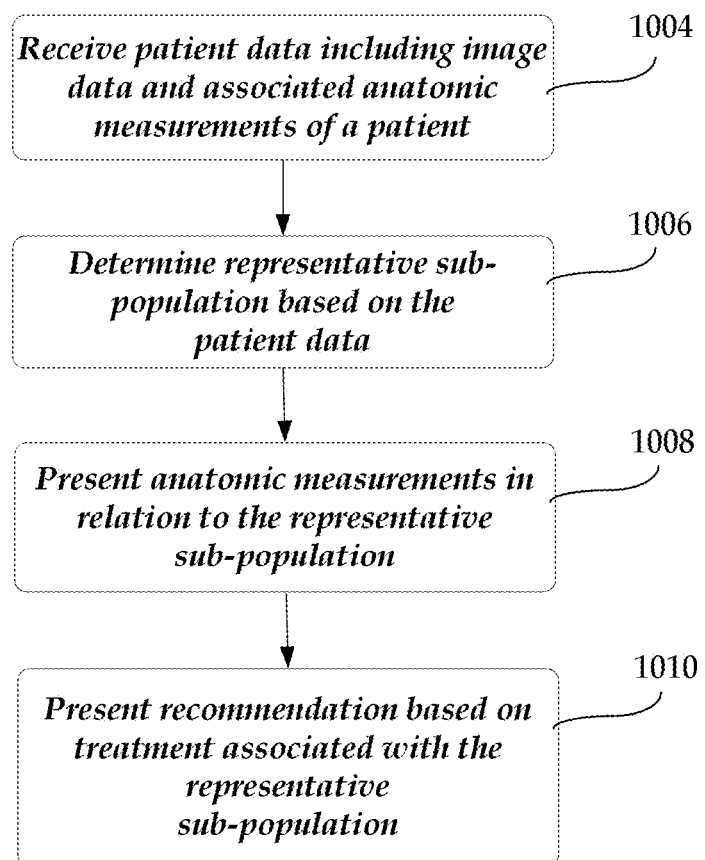
FIG. 10 shows an exemplary method of generating a report by a computer system.

FIG. 10 shows an exemplary method 1000 of generating a report by a computer system. It should be understood that the steps of the method 1000 may be performed in the order shown or a different order. Additional, different, or fewer steps may also be provided. Further, the method 1000 may be implemented with the system 101 of FIG. 1, a different system, or a combination thereof.

At 1004, report generator 108 receives patient data of a given patient. The given patient may be, for example, a patient currently undergoing examination, evaluation or therapy (or treatment) by a physician. The patient data may include image data of a structure of interest and associated anatomic measurements, as well as other patient information (e.g., age, ethnicity, gender, risk factor, laboratory test analysis results). The structure of interest may be, for example, a tubular structure (e.g. vascular structure, airway, urinary track, etc.), a bone structure (e.g., femur, skull, ribs, spine, etc.), nerves, etc. The image data may be acquired by, for example, imaging device 102, using techniques such as magnetic resonance (MR) imaging, computed tomography (CT), helical CT, X-ray, angiography, positron emission tomography (PET), fluoroscopy, ultrasound, single photon emission computed tomography (SPECT), or a combination thereof.

The anatomic measurements may one-dimensional, two-dimensional, three-dimensional, or other dimensional. The anatomic measurements may have been performed on image data either manually, semi-automatically or automatically. In some implementations, the anatomic measurements are automatically performed by measurement tool 106. For example, the measurements may be performed to determine the degree of spondylolisthesis, as previously described with reference to FIG. 2. It should be appreciated that other types of measurements, such as diameter, length, thickness, area, volume, flow, change, and/or rate of change of measurements, may also be determined. The measurements may also be determined based on relationships between different measurements, including but not limited to, angles, ratios, and so forth.

Figure 11:
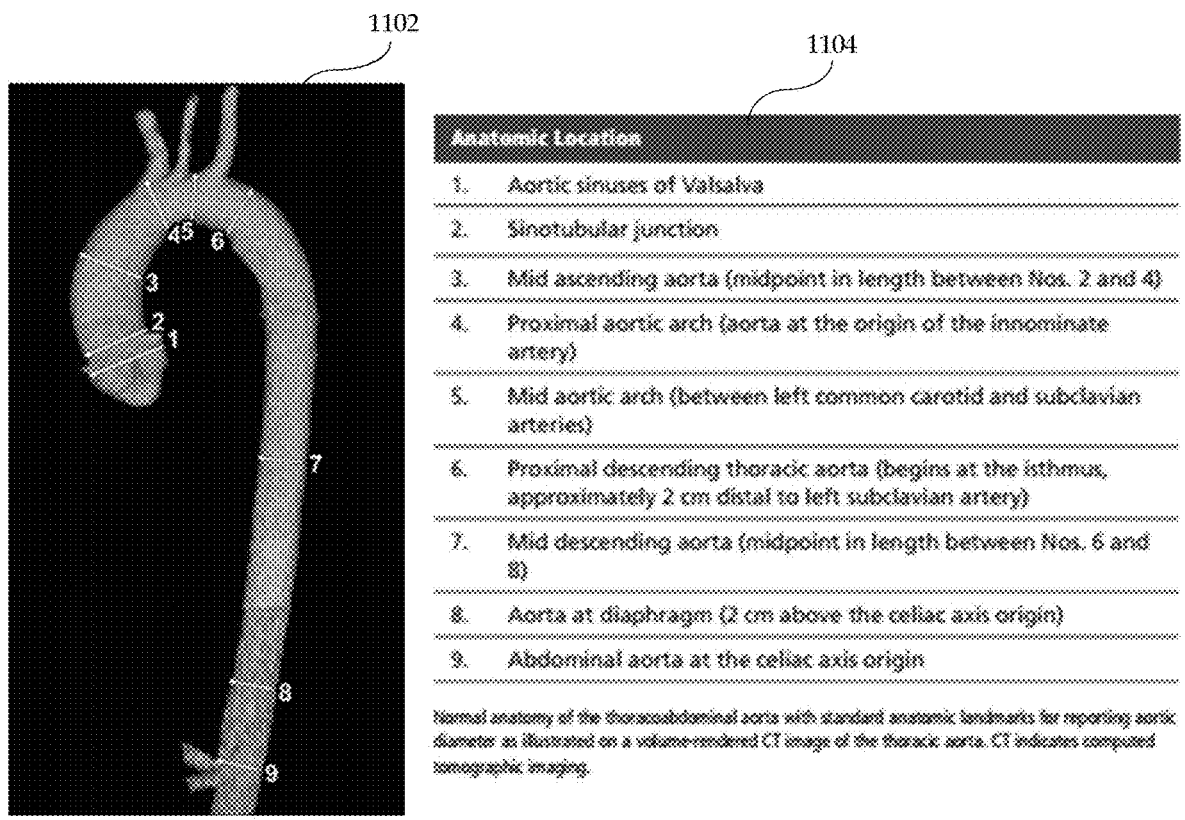
FIG. 11 show exemplary anatomic landmark locations according to the American College of Cardiology (ACC) and the American Heart Association (AHA) guidelines for diagnosis and management of patients with thoracic aortic disease.

In some implementations, the anatomic measurements are performed at pre-defined anatomic landmark locations according to well-established guidelines. FIG. 11 show exemplary anatomic landmark locations according to the ACC/AHA guidelines for diagnosis and management of patients with thoracic aortic disease. Volume-rendered CT image 1102 shows the normal anatomy of a thoracoabdominal aorta with pre-defined anatomic landmarks 1-9 for measuring aortic arch diameters. Table 1104 describes the corresponding locations of the anatomic landmarks 1-9.

The anatomic measurements may also be performed at a continuum of locations, including the pre-defined anatomic landmark locations, throughout the structure of interest. Continuum of measurements is of importance when measurements are performed to capture the onset of the disease. In the context of aortic diameters, for example, the measurements are performed to capture the potential onset of aortic dissection. However, actual enlargement of aorta may be manifested at a higher or different location than where the diameter is measured according to guidelines. For example, when measuring the mid ascending diameter over time to detect enlargement, an actual enlargement located between the proximal descending thoracic aorta (6) and mid descending aorta (7) (as shown in FIG. 11) may be missed if the diameters are measured only at positions (6) and (7). In addition to the measurements at the prescribed locations, a diameter profile for the whole length of the aorta highlighting areas which are out of bounds from normal diameter may be presented to the physician to facilitate early identification of the onset of disease.

Returning to FIG. 10, at 1006, report generator 108 determines a sub-population of patient records from the database 109 that best represents the patient. The database 109 may have been previously clustered into pre-defined sub-populations by database builder 107, as previously described with reference to FIG. 8. Atlases may be created for specific sub-populations to capture the underlying characteristics of the cluster and making it easier to relate a measurement for a given patient to the whole sub-population. The representative sub-population may be selected by finding the sub-population that is most similar to the given patient by matching patient characteristics and anatomic measurements extracted from the patient data with those associated with each sub-population.

At 1008, report generator 108 generates a report that presents the anatomic measurements in relation to the representative sub-population. In some implementations, report generator 108 automatically associates the patient's anatomic measurements with corresponding labeled anatomic measurements extracted from the patient records in the representative sub-population. Report generator 108 may compare the patient's measurements with the extracted measurements to identify differences between the patient and the sub-population and present such differences in the report. The patient's measurements may also be compared with each other to identify any lack of symmetry, anomaly or difference from other similar anatomic structures within the patient's body (e.g. vertebral height, vertebral listhesis, vascular diameter, etc.). Any differences or anomalies may be manifested or highlighted in the report to facilitate discovery of a latent form or possible early onset of a clinical condition or disease in patients who may be asymptomatic for that particular condition or disease (e.g., vertebral listhesis, aortic dissection, etc.). Additionally, anomalies may be automatically correlated with medical publications or knowledge to enable evidence-based identification of a condition or disease.

Figure 12:
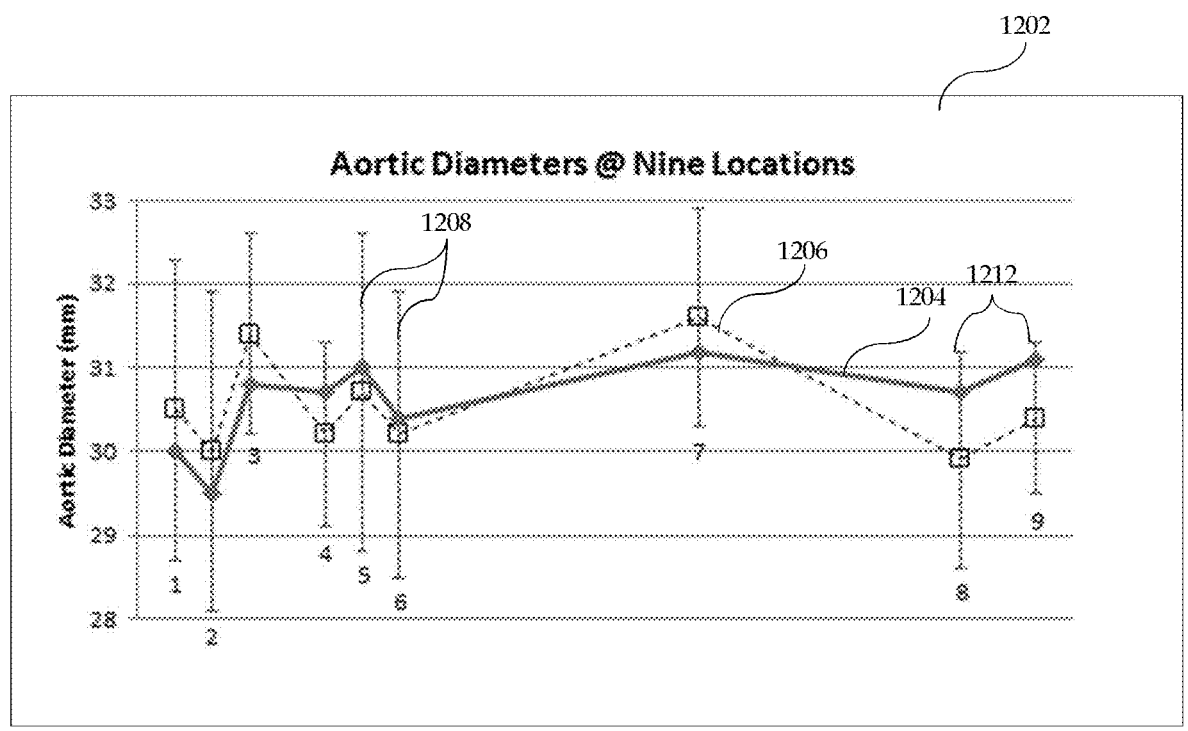
FIG. 12 illustrates an exemplary chart in a summary view.

In some implementations, report generator 108 presents a summary view that represents the anatomic measurements at pre-defined anatomic landmarks in a concise form. FIG. 12 illustrates an exemplary chart 1202 in a summary view. Average aortic diameter values measured at various anatomic landmark locations 1-9 are connected by the solid line 1204. Vertical error bars 1208 represent the maximum and minimum measurement values at each location for the population representative of the patient. Average aortic diameter values associated with the sub-population representative of the given patient are connected by the dotted line 1206.

It can be observed that most of the diameters 1204 are close to the average diameters 1206 of the representative sub-population, the diameters at locations 8 and 9 are of clinical concern as they are much closer to the upper bounds 1212 of the measurement variation for the representative sub-population. Hence, while the physician may likely want to monitor all measurement values over time, he or she may pay particular attention not only to measurements at locations 8 and 9, but also in the aorta area, since the measurement values are proxies for the actual aortic diameters for capturing the underlying onset of the disease. An "alarm" mechanism may be provided to generate an alert when measurements exceed the norm (or threshold) or are too close to a boundary. This may help in making sure that these events are noted. The mechanism may be automated to facilitate processing of hundreds of measurements.

Figure 13:
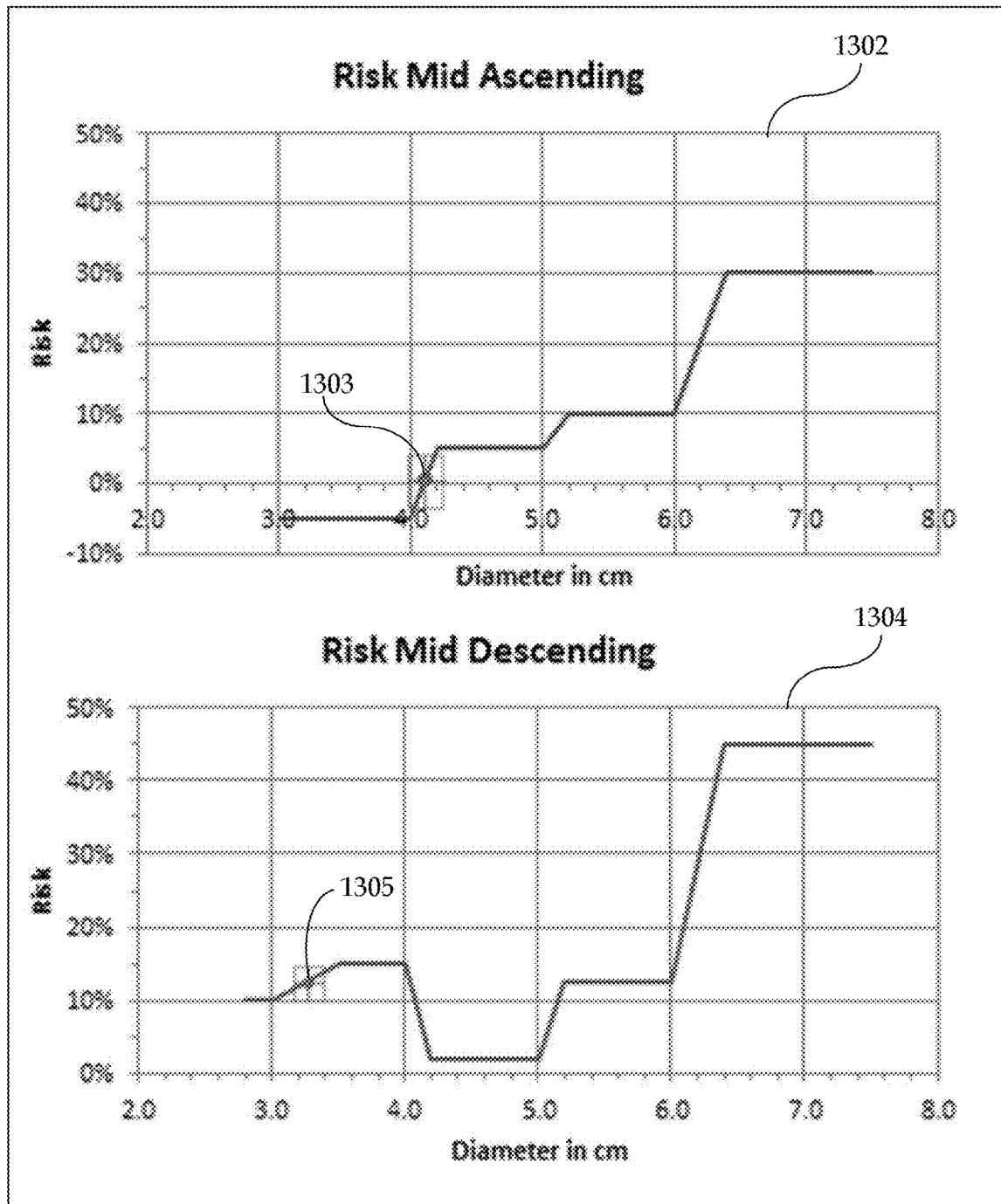
FIG. 13 illustrates the influence of aortic size on cumulative and lifetime incidences of natural complications of aortic aneurysm.

The risk of dissection may be related to the diameter of the aorta. See, for example, Erbel R, Eggebrecht H, "Aortic dimensions and the risk of dissection," *Heart*, 2006; 92(1): 137-142, which is herein incorporated by reference. In some implementations, report generator 108 presents the measurements in relation to associated risk levels. FIG. 13 illustrates the influence of aortic size on cumulative and lifetime incidences of natural complications of aortic aneurysm. Exemplary graphs 1302 and 1304 are shown to illustrate the risk of complication at the mid-ascending and mid-descending respectively. Each graph (1302, 1304) plots the risks of complication (in percentage) for aortic dissection against the average diameter (in centimeters) at a given location for a particular individual. The age of the patient is accounted for in the computation of risk. The risk level for the current patient is exemplified by the dot (1303, 1305).

Figure 14A:
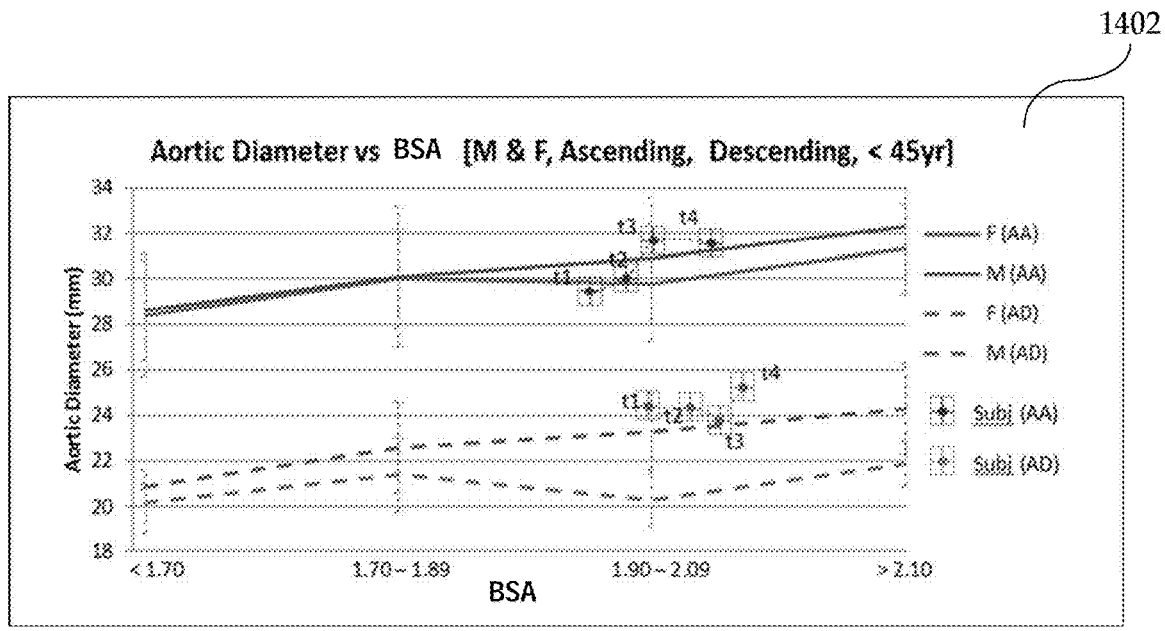
FIG. 14a shows a chart depicting measurements of aortic diameter as a function of body surface area (BSA)

Report generator 108 may also generate a report that relates anatomic measurements to patient-specific characteristics (e.g., age, gender, body surface area or BSA, etc.) of the given patient and the representative sub-population to facilitate identification of observable trends following subsequent examination. FIG. 14a shows a chart 1402 depicting measurements of aortic diameter (in millimeters) as a function of BSA. The measurements are made with consideration of Gender (F: female or M: male), at Age<45 yrs and 4 locations (A: ascending or D: descending). See, for example, WANG Y-L, WANG Q-L, WANG L, et al., "Body surface area as a key determinant of aortic root and arch dimensions in a population-based study," *Experimental and Therapeutic Medicine*. 2013; 5(2):406-410; and Pearce et al., "Aortic diameter as a function of age, gender, and body surface area," Surgery, 1993 October; 114(4):691-7, which are all herein incorporated by reference. More particularly, the solid lines (F(AA) and M(AA)) represent the female and male functions at the AA location respectively, while the broken lines (F(AD) and M(AD)) represent the female and male functions at the AD location respectively. The points denoted by Subj(AA) and Subj(AD) represent the relative measurements of aortic diameters as a function of BSA for a given patient measured at two locations (AA and AD) tracked over time (t1, t2, t3, t4).

Figure 14B:
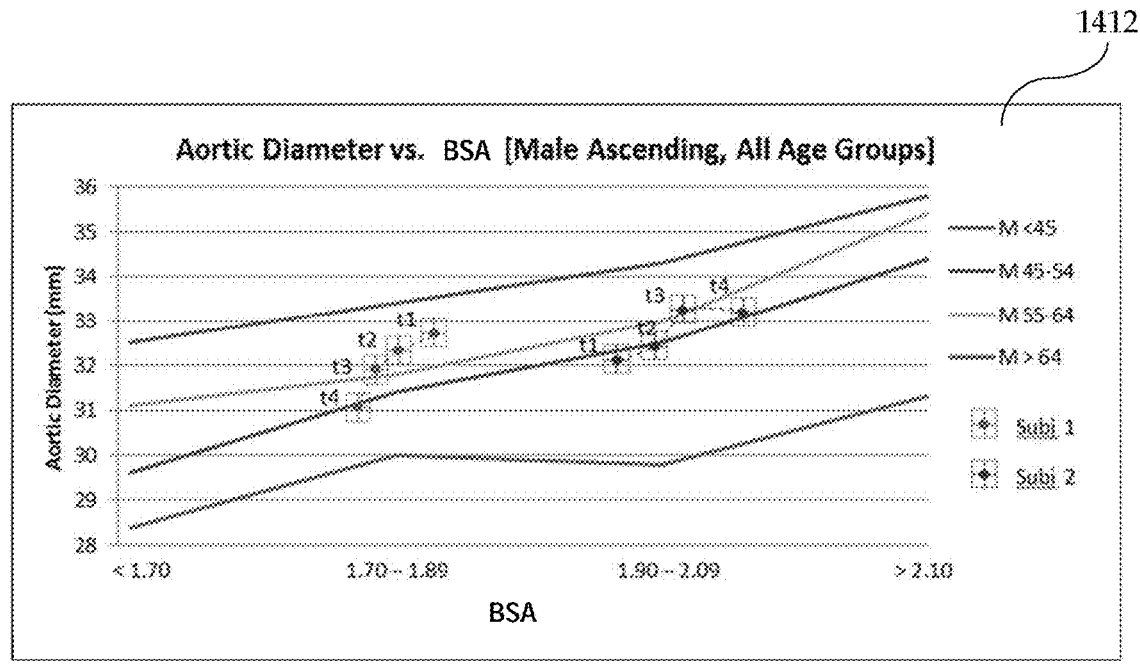
FIG. 14b shows a chart depicting measurements of aortic diameter as a function of BSA at the ascending location for male patients.

FIG. 14b shows a chart 1412 depicting measurements of aortic diameter (in millimeters) as a function of BSA at the ascending location for male patients (M) with consideration for different age groups (<45, 45-54, 55-64, >64). The points denoted by Subj 1 and Subj 2 represent the relative measurements of aortic diameters (at a given location AA) as a function of BSA for two individual patients tracked over time (t1, t2, t3, t4).

Measurements may change not only due to pathology, but also as a byproduct of aging. See, for example, O'Rourke M, Farnsworth A, O'Rourke J. Aortic, "Dimensions and Stiffness in Normal Adults," *J Am Coll Cardiol Img,* 2008; 1(6):749-751, which is herein incorporated by reference. For example, the ascending aorta of a 20-year-old patient may be compared with the ascending aorta of an 80-year-old man. The length of the ascending aorta may increase by approximately 12% per decade, and the diameter may increase by 3% per decade. By considering specific patient characteristics (e.g., age), the information extracted and summarized for a sub-population may be used to account for anatomic changes associated with aging.

At 1010, report generator 108 generates a report that presents one or more recommendations for treatment (or therapy) associated with the representative sub-population. Report generator 108 may present treatment options with the best outcomes associated with the particular sub-population representative of the given patient by using the mapping information relating the sub-population to the treatment and associated outcomes (as previously described with reference to FIG. 8). Effectiveness of treatment (or therapy) may be advantageously assessed at an earlier stage by being able to identify the given patient within a sub-population. The individual risk associated with the given patient may also be determined.

Additionally, report generator 108 may extract recommendations of the most suitable treatment given the measurements from published peer-reviewed journal literature and/or clinical data. Such publications may be stored in, for example, database 109 or additional databases, and mapped to one or more specific sub-populations to be available as evidence-based documentation accessible to a physician when determining the therapy plan.

In some implementations, the report containing measurements and/or recommendations for treatment is presented in a dashboard or dashboard-like environment for performing informed patient management based on evidence. The report may be presented at, for example, workstation 103. The dashboard may allow the physician to explore various therapy or treatment scenarios by modifying the patient's characteristics (e.g. to simulate the event whereby the patient reduces cholesterol or weight), or by simulating positive or negative responses to a drug (e.g., side effects which are presently unknown for a specific patient). The dashboard may further enable input of intermediary results from the treatment plan and present the impact on the possible outcome for the particular patient.

The dashboard may enable an interactive workflow that allows an efficient review of anomalous anatomy with potential indication of an associated condition or disease. The dashboard may enable the user to not only review individual measurements relative to a sub-population, but also to define relevance thresholds for filtering the measurements. For example, when reviewing a complete spine for spondylolisthesis, the user may request to see only measurement values and changes that are above a certain tolerance value, e.g. 5% or 3 mm. This may greatly simplify the review process and not force the user to review every single vertebra along the spine.

The dashboard may further notify or alert the physician of a change in the disease or condition (e.g., worsened, stabilized or improved) subject or not-subject to therapy. An overall view of all the measurements may be presented using color coding or other visual mapping to indicate changes (e.g., blue indicates no change; red indicates significant change). The relevance of the change may be derived from published literature or institution-specific guidelines and presented on the dashboard. The change in condition may be considered with respect to other comorbidities or conditions in the patient (or other similar patients in the representative sub-population) and may contribute as a risk factor for the current or other disease. For example, quantification of change in plaque in the aorta, blood pressure, level of cholesterol or calcium scoring in the coronaries, may be used to determine a change in the risk of heart attack occurrence.

The patient may be provided access to the dashboard to view his or her own health status, and/or update or upload information from a mobile device or network connected device to monitor blood pressure, weight, sugar level, or other assay available to commercially available platforms. The patient or physician may also link other members of the patient's family to provide input to enhance the patient's profile, thus enabling better tailoring of therapy and refinement of subpopulation characterization.

Recommendations for treatments may be filtered based on the medical cost payer's (e.g., insurance company's) reimbursement plans. While a patient may undergo multiple treatment plans to reach the same outcome or various outcomes, payers may endorse only some of the available therapies. Based on the patient-specific insurance coverage, for example, the dashboard may present only treatments that are covered by the reimbursement plan of a medical cost payer (e.g., insurance plan).

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A non-transitory computer readable medium embodying a program of instructions executable by machine to perform operations for anatomic measurement, the operations comprising:
  receiving image data of at least a portion of a spine of a patient;
  applying a machine learning technique comprising a deep learning algorithm to determine centroids, vertebra-center coordinate systems or vertebra-specific landmarks of a target vertebra and an adjacent vertebra of the spine in the image data and automatically measuring an anterior shift of the target vertebra of the spine based on the centroids, the vertebra-center coordinate systems or the vertebra-specific landmarks, wherein the anterior shift is automatically measured by identifying first and second front planes of the target vertebra and the adjacent vertebra respectively or first and second back planes of the target vertebra and the adjacent vertebra respectively and determining a distance between the first and second front planes or the first and second back planes, wherein the first and second front planes or the first and second back planes are perpendicular to a spinal disc between the target and the adjacent vertebrae, wherein the anterior shift is an acquired anterior displacement of the target vertebra relative to the adjacent vertebra;
  determining a degree of spondylolisthesis based on the anterior shift; and
  presenting the degree of spondylolisthesis in relation to a representative sub-population of patients similar to the patient in a report.

2. The non-transitory computer readable medium of claim 1, wherein the instructions are executable by the machine to automatically measure another anterior shift by
  determining a relative displacement of the target vertebra with respect to the adjacent vertebra based on the centroids, vertebra-center coordinate systems or vertebra-specific landmarks of the target vertebra and the adjacent vertebra of the spine.

3. The non-transitory computer readable medium of claim 1, wherein the instructions are executable by the machine to automatically measure another anterior shift by
  characterizing an overall profile of the spine, and
  determining the another anterior shift based on deformation of the overall profile.

4. The non-transitory computer readable medium of claim 1, wherein the instructions are executable by the machine to automatically measure another anterior shift by segmenting the target vertebra and the adjacent vertebra of the spine.

5. The non-transitory computer readable medium of claim 4, wherein the instructions are executable by the machine to segment the target and adjacent vertebrae by
  automatically detecting pre-defined landmarks of the spine using a machine-learning technique, and
  extracting, based on the detected landmarks, a region of interest containing the target or adjacent vertebra of the spine.

6. The non-transitory computer readable medium of claim 4, wherein the instructions are executable by the machine to automatically measure another anterior shift by
  identifying a first most anterior point and a first most posterior point of a lower or upper surface of the target vertebra,
  identifying a second most anterior point and a second most posterior point of an upper or lower surface of the adjacent vertebra,
  projecting the first most posterior point to the upper or lower surface of the adjacent vertebra to generate a projected point, and
  calculating the another anterior shift by determining a first distance between the projected point and the second most posterior point.

7. The non-transitory computer readable medium of claim 6, wherein the instructions are executable by the machine to determine the degree of spondylolisthesis by
  determining a slippage based on a ratio of the anterior shift to a second distance between the second most anterior point and the second most posterior point, and
  assigning, according to a Meyerding grading system, a grade of spondylolisthesis based on the slippage.

8. The non-transitory computer readable medium of claim 1, wherein the instructions are executable by the machine to determine the representative sub-population of patients similar to the patient based on the degree of spondylolisthesis, wherein the representative sub-population is selected from a previously clustered database.

* * * * *